US009707371B2

(12) United States Patent
Callaghan et al.

(10) Patent No.: US 9,707,371 B2
(45) Date of Patent: Jul. 18, 2017

(54) VENTILATION SYSTEMS AND METHODS

(75) Inventors: Matthew John Callaghan, Stanford, CA (US); William Bishop, Palo Alto, CA (US); Lawrence Edward Miller, Mountain View, CA (US); Peter Frykman, Palo Alto, CA (US); Francois Brahic, Mountain View, CA (US)

(73) Assignee: The Board of Trustees of the Leland Stanford, Jr. University, Stanford, CA (US)

( * ) Notice: Subject to any disclaimer, the term of this patent is extended or adjusted under 35 U.S.C. 154(b) by 1074 days.

(21) Appl. No.: 13/469,058

(22) Filed: May 10, 2012
(Under 37 CFR 1.47)

(65) Prior Publication Data
US 2013/0087146 A1 Apr. 11, 2013

Related U.S. Application Data

(63) Continuation of application No. PCT/US2010/056428, filed on Nov. 11, 2010.
(Continued)

(51) Int. Cl.
*A61M 16/00* (2006.01)
*F16K 31/02* (2006.01)
(Continued)

(52) U.S. Cl.
CPC ......... *A61M 16/208* (2013.01); *A61M 16/00* (2013.01); *A61M 16/0063* (2014.02);
(Continued)

(58) Field of Classification Search
None
See application file for complete search history.

(56) References Cited

U.S. PATENT DOCUMENTS 4,232,668 A 11/1980 Strupat
4,681,099 A * 7/1987 Sato ............... A61M 16/00
128/204.23
(Continued)

FOREIGN PATENT DOCUMENTS

JP 04-1764672 6/1992
JP 2005-152615 6/2005
JP 2006-122077 5/2006

OTHER PUBLICATIONS

Patent communications for corresponding national application in Singapore: Singapore Patent Application No. 201203421-2 including Search Report and Written Opinion: May 20, 2014, 16 pgs., Response to Search Report: Nov. 13, 2014, 8 pgs., and Subsequent Examination Report: Dec. 31, 2014, 11 pgs.
(Continued)

*Primary Examiner* — Tan-Uyen T Ho
*Assistant Examiner* — Eric Bryant
(74) *Attorney, Agent, or Firm* — William A. English; Vista IP Law Group LLP

(57) ABSTRACT

A ventilator includes a compressor, a storage vessel, a valve assembly communicating with the compressor, the storage vessel, and an inhalation line. A controller directs the valve assembly between a storage configuration where ventilation gas is delivered from the compressor into the storage vessel, and a delivery configuration where ventilation gas is delivered from the storage vessel to the inhalation line. The controller is coupled to a pressure sensor for detecting a first pressure within the storage vessel when the valve assembly is directed to the delivery configuration, and detecting subsequent pressure while ventilation gas is delivered from the storage vessel to the inhalation line, the controller determining the volume of ventilation gas delivered to the (Continued)

patient based at least in part on the difference between the first pressure and the subsequent pressure.

31 Claims, 5 Drawing Sheets

Related U.S. Application Data

(60) Provisional application No. 61/260,296, filed on Nov. 11, 2009.

(51) Int. Cl.
    *A61M 16/20*     (2006.01)
    *A61M 16/12*     (2006.01)

(52) U.S. Cl.
    CPC ........ *A61M 16/204* (2014.02); *A61M 16/205* (2014.02); *A61M 16/12* (2013.01); *A61M 2016/0021* (2013.01); *A61M 2205/3351* (2013.01); *A61M 2205/3358* (2013.01); *A61M 2205/502* (2013.01); *A61M 2205/8206* (2013.01)

(56) References Cited

U.S. PATENT DOCUMENTS

| | | | | |
|---|---|---|---|---|
| 4,815,452 A | * | 3/1989 | Hayek | 601/44 |
| 4,838,261 A | | 6/1989 | von dem Hagen | |
| 5,237,987 A | * | 8/1993 | Anderson et al. | 128/204.18 |
| 5,383,449 A | | 1/1995 | Forare et al. | |
| 5,558,083 A | * | 9/1996 | Bathe et al. | 128/203.12 |
| 5,839,434 A | * | 11/1998 | Enterline | 128/204.23 |
| 6,393,802 B1 | * | 5/2002 | Bowser | F17C 5/002 53/403 |
| 7,402,193 B2 | * | 7/2008 | Bliss | B01D 53/0407 128/204.26 |
| 2002/0144683 A1 | | 10/2002 | Gurnee et al. | |
| 2003/0121561 A1 | * | 7/2003 | Wagner | B01F 15/00194 141/9 |
| 2004/0079359 A1 | | 4/2004 | Aylsworth et al. | |
| 2005/0139214 A1 | | 6/2005 | Yagi et al. | |
| 2006/0249153 A1 | * | 11/2006 | DeVries | A61M 16/0057 128/204.18 |
| 2007/0068518 A1 | * | 3/2007 | Urias | A61M 16/00 128/200.24 |
| 2007/0129646 A1 | * | 6/2007 | Heinonen et al. | 600/532 |
| 2007/0144523 A1 | * | 6/2007 | Bolam et al. | 128/205.24 |
| 2008/0092891 A1 | * | 4/2008 | Cewers | 128/204.18 |
| 2008/0105258 A1 | * | 5/2008 | Deane | B01D 53/053 128/204.21 |
| 2009/0071478 A1 | * | 3/2009 | Kalfon | A61M 16/0051 128/204.17 |
| 2010/0300446 A1 | * | 12/2010 | Nicolazzi | A61M 16/208 128/205.24 |
| 2011/0146681 A1 | * | 6/2011 | Jafari et al. | 128/204.21 |
| 2011/0197822 A1 | * | 8/2011 | Chou | A01K 1/0254 119/496 |
| 2011/0259334 A1 | * | 10/2011 | Alfieri | A61M 16/0051 128/205.12 |

OTHER PUBLICATIONS

Patent communications for corresponding national application in Japan: Japanese Patent Application No. 2012-538993, including Office Action/translation: Aug. 14, 2014, 8 pgs., and Response: Feb. 12, 2015, 16 pgs.
Supplemental Search Report for corresponding regional application in Europe: European Patent Application No. 10830751.3, Jul. 14, 2015, 5 pgs.
Examination Report for corresponding national application in Australia: Australian Patent Application No. 2010319481, Apr. 14, 2015, 5 pgs.
International Search Report and Written Opinion from corresponding PCT application: PCT/US2010/056428, Jul. 27, 2011, 15 pgs.

* cited by examiner

VENTILATION SYSTEMS AND METHODS

RELATED APPLICATION DATA

The present application is a continuation of co-pending International Application No. PCT/US2010/056428, filed Nov. 11, 2010, which claims benefit of U.S. provisional application Ser. No. 61/260,296, filed Nov. 11, 2009, the entire disclosures of which are expressly incorporated by reference herein.

FIELD OF THE INVENTION

The present invention relates generally to ventilators and systems and methods of ventilation for humans and other animals. More particularly, the present invention relates to ventilators that may be built with minimal resources, allowing for inexpensive mass production.

BACKGROUND

Surge capacity mechanical ventilation during an influenza pandemic requires devices capable of positive pressure ventilation ("PPV") and delivery of positive end expiratory pressure ("PEEP"). The duration of disease may last from days to weeks, and mechanical ventilation may be required for greater than one week. One of the most dangerous results of a severe influenza infection is acute respiratory distress syndrome ("ARDS"). ARDS, which is the most frequent severe complication of influenza, is characterized by diffuse inflammation of the lungs leading to impaired gas exchange.

Currently marketed ventilators range from costly, sophisticated machines to simple low cost transport devices. Patients with ARDS need advanced ventilators capable of PPV and PEEP to overcome the increased alveolar collapse caused by inflammation. Currently marketed full-featured machines are prohibitively expensive, fragile, and overly complex for use by less skilled personnel. Portability and durability are limited and a constant power supply is required. These features make full-featured machines unsuitable for use in field settings, rural areas, or in a large scale emergency situation such as a pandemic.

Currently marketed transport ventilators are designed to be used as a temporary bridge during patient travel to and from a full-featured ventilator. Although they are more portable than the full featured ventilators, transport ventilators are not appropriate for use in ARDS patients during a pandemic. They often do not provide PEEP, have no spontaneous assist mode and are not approved for critical care use. Inefficient use of compressed air and electricity also make them ill-suited for low-resource environments and developing nations.

Low-cost resuscitators are currently available for under two hundred dollars ($200). These devices are designed as a last resort in acute situations and require constant direct supervision. They are generally not used to support an ARDS patient for any clinically relevant length of time.

When considered on a global scale, the disparity in pandemic resources between wealthy and impoverished nations is alarming. With the majority of the world's vaccine supply already purchased by wealthy nations, coverage in developing nations may be inadequate. Many countries already face an extreme shortage of ventilators, even in the absence of a pandemic. For example, in the United States, there are approximately 205,000 ventilators for a population of 300 million. In India, where the population exceeds 1.1 billion, there are only 35,000 intensive care ventilators available. What is needed to address this disparity is an extremely low-cost ventilator, specifically tailored to meet the needs of acute respiratory distress patients in low-resource, rural and emergency environments.

SUMMARY OF THE INVENTION

The present invention is directed generally to ventilators and systems and methods of ventilation for humans and other animals. For example, the ventilators described herein may be built with minimal resources, e.g., allowing for inexpensive mass production.

In accordance with an exemplary embodiment, a ventilation system is provided that includes a source of pressurized gas; a patient vessel; a first pressure sensor coupled to the patient vessel for detecting the pressure of ventilation gas within the patient vessel; and a valve assembly, e.g., including one or more valves, communicating with the gas source via a source line, the patient vessel, and an inhalation line for delivering ventilation gas to a patient. A controller may be coupled to the valve assembly for selectively directing the valve assembly between a storage configuration where ventilation gas is delivered from the gas source into the storage vessel, and a delivery configuration where ventilation gas is delivered from the storage vessel to a patient via the inhalation line. The controller may also be coupled to the first pressure sensor for detecting a first pressure within the storage vessel when the valve assembly is directed to the delivery configuration, and detecting subsequent pressure thereafter while ventilation gas is delivered from the storage vessel to the patient via the inhalation line, the controller determining the volume of ventilation gas delivered to the patient based at least in part on the difference between the first pressure and the subsequent pressure.

In accordance with another embodiment, a ventilator is provided that includes a source of pressurized gas; a pre-fill vessel; a patient vessel; a valve assembly communicating with the gas source via a source line, the pre-fill and patient vessels, and an inhalation line for delivering ventilation gas to a patient; and a controller coupled to the valve assembly for selectively directing the valve assembly between a delivery configuration where ventilation gas is delivered from the patient vessel to a patient via the inhalation line and pressurized gas is delivered from the gas source to the pre-fill vessel, and a storage configuration where pressurized gas is delivered from the gas source and the pre-fill vessel into the storage vessel to store pressurized gas in the storage vessel.

In accordance with yet another embodiment, a method for ventilating a patient is provided that includes placing the patient's airway in fluid communication with an inhalation line of a ventilator, the ventilator including a storage vessel therein and a source of pressurized gas. Ventilation gas is delivered from the gas source into the storage vessel during a storage phase, and ventilation gas is delivered from the storage vessel to the patient via the inhalation line during a delivery phase. During the delivery phase, the change in pressure in the storage vessel may be measured, e.g., to determine a volume of pressurized gas being delivered to the patient from the storage vessel. The ventilator may be operated based at least in part on the change in pressure in the storage vessel independent of the duration of the inhalation phase and/or based at least in part on the change in pressure in the storage vessel without measuring a flow rate of ventilation gas delivered to the patient.

In accordance with still another embodiment, a method for ventilating a patient is provided that includes performing the following steps one or more times sequentially: a) delivering ventilation gas from a storage vessel within a ventilator to the patient via an inhalation line with the storage vessel isolated from a gas source of the ventilator; b) measuring the change in pressure in the storage vessel while ventilation gas is delivered to the patient from the storage vessel; c) determining the volume of ventilation gas delivered to the patient based at least in part on the change in pressure; d) discontinuing delivery of ventilation gas from the storage vessel to the patient; and e) delivering ventilation gas from the gas source into the storage vessel to refill the storage vessel with pressurized gas.

In one embodiment, measuring the change in pressure may include measuring a first pressure in the storage vessel before or immediately after beginning to deliver ventilation gas to the patient from the storage vessel; and measuring pressure in the storage vessel at predetermined time intervals thereafter while ventilation gas is delivered to the patient, the volume of ventilation gas delivered to the patient being determined based at least in part on the difference between the first pressure and the subsequent pressure. For example, the cumulative volume of ventilation gas delivered during each time interval may be compared to a predetermined maximum volume, and the delivery of ventilation gas from the storage vessel to the patient may be discontinued when the estimated cumulative volume meets or exceeds the predetermined maximum volume. In another embodiment, the pressure within the storage vessel may be monitored while ventilation gas is delivered to the patient from the storage vessel to determine a derivative of the pressure with respect to time until the derivative drops to a predetermined threshold approaching zero, whereupon delivery may be discontinued.

In accordance with yet another embodiment, a ventilator is provided that includes a housing; a source of pressurized ventilation gas; a valve within the housing to control the flow of ventilation gas to a patient via an inhalation line; and a flow restrictor for limiting a flow rate of ventilation gas from the compressor to the patient, the flow restrictor located after the valve in the inhalation line. The flow restrictor may be manually adjustable for changing a maximum flow rate deliverable through the inhalation line to a patient and/or may be decoupled from a controller controlling the valve.

In accordance with still another embodiment, a ventilator is provided that includes a housing; a source of pressurized ventilation gas; and one or more valves within the housing communicating with the gas source and an inhalation line for delivering ventilation gas to a patient, the one or more valves operable only in either a fully opened or a fully closed state to control the flow of ventilation gas to the patient.

In accordance with yet another embodiment, a method for ventilating a patient is provided that includes placing the patient's airway in fluid communication with an inhalation line of a ventilator; operating a compressor within the ventilator substantially continuously for generating a substantially continuous stream of pressurized gas within the ventilator; intermittently delivering pressurized gas from the ventilator to the patient; and storing at least a portion of the stream of pressurized gas from the compressor within the ventilator.

In one embodiment, at least a portion of the stream of pressurized gas may be stored within a patient vessel within the ventilator, and wherein the pressurized gas intermittently delivered to the patient is delivered from the patient vessel. For example, the ventilator may divert a portion of the stream of pressurized gas to a pre-fill vessel when the pressurized gas is delivered to the patient from the patient vessel. At least a portion of the stream of pressurized gas diverted to the pre-fill vessel may be delivered into the patient vessel when at least a portion of the stream of pressurized gas is being stored in the patient vessel to increase the volume and/or pressure of pressurized gas stored in the patient vessel.

For example, the compressor may generate a substantially continuous stream of pressurized gas at a flow rate between about eight and twelve liters per minute (8-12 lpm). In another example, the portion of the stream of pressurized gas stored within the patient vessel may create a peak internal pressure within the patient vessel of at least 350 cc H2O (5 psi), at least 700 cc H2O (10 psi), or at least 1100 cc H2O (15 psi). In yet another example, the maximum pressure in the inhalation line during delivery of ventilation gas to the patient may be 70 cc H2O (1 psi). In addition or alternatively, the ratio of the peak internal pressure within the patient vessel and the maximum pressure in the inhalation line is at least two (2) or five (5).

In accordance with yet another embodiment, a ventilation system is provided that includes a pressure source, a first valve (e.g., solenoid valve assembly), a first actuator configured to activate the first valve, and a conduit. The first valve may be electronic and may use from about 1.2 W to about 4.8 W during regular operation. The controller may apply an initially larger voltage across the valve while the valve is opening, e.g. to speed its opening, and then may reduce the voltage to hold the valve open, e.g., to decrease the power consumption of the valve. The ventilation system may be configured to be attached to the pressure source. For example, the pressure source may be a central air pressure supply line (e.g., passed through the walls of a health care facility), to which the ventilation system may be coupled, a substantially constant volume pressure vessel (e.g., a pressurized air tank), and/or an internal or external compressor to which the ventilation system may be coupled.

The ventilation system may include one or more solenoid assemblies. For example, the solenoid assembly may have a first actuator that may have a first solenoid. The ventilation system may also have a second valve (e.g., an exhale valve). The first actuator may be configured to activate the first valve and/or the second valve. The solenoid assembly may have a second solenoid that may actuate a second valve. In different settings, the solenoid valve assembly may route air from the pressure source to one or more pressure vessels (i.e., recharging the pressure vessels) and/or from the pressure vessels to an inhalation line to the patient.

The solenoid valve assembly may control the flow of a large volume of air, e.g., by a small electromagnetic valve requiring low power, for example, less than about three Watts (3 W), or less than or equal to about 1.6 W.

The system may be operated in one or more different modes, as desired, e.g., controlled between Control Mode Ventilation (i.e., "CMV"), Assist-Control ("A-C") and continuous positive airway pressure ("CPAP"), and/or bilevel positive airway pressure ("BiPAP") modes.

In accordance with another embodiment, a ventilation system for ventilating a patient may be provided that includes a pressure source, a first pressure vessel, a second pressure vessel, and a conduit configured to lead to the patient. The device may have a first valve, and the pressure source may be in fluid communication with the pressure conduit via the first valve. The pressure source may be in fluid communication with the conduit.

In accordance with yet another embodiment, a method is provided for ventilating a patient that may include placing the patient's airway in fluid communication with a ventilator that may have a pressure vessel. The method may include measuring the change in pressure in the pressure vessel. The method may include activating the ventilator based at least in part on the change in pressure in the pressure vessel. For example, the ventilator may be operated without measuring flow rate and the duration of various phases of operation, e.g., delivery or inhalation phase and/or storage or exhalation phase.

The method may include delivering a gas from the pressure vessel to the patient's airway. The pressure vessel may be a rigid, fixed volume structure, such as a gas tank. The pressure in the pressure vessel may decrease during the delivering of the gas to the patient's airway, and the method may include determining a volume of gas discharged from the pressure vessel by measuring the change in pressure in the pressure vessel. The method may include displaying a volume of gas discharged from the pressure vessel on an output device, e.g., a display or other user interface.

In accordance with still another embodiment, a method is provided for ventilating a patient that may include placing the patient's airway in fluid communication with a ventilator. The ventilator may include a pressure vessel, and the method may include measuring the change in pressure in the pressure vessel. The method may include activating the ventilator based at least in part on the change in pressure in the pressure vessel.

The systems and methods provided herein may offer the clinical functionality of a sophisticated ICU or transport machine at a price that may be an order of magnitude lower than other systems. Further, the systems and methods herein may operate with minimal power and/or no external or compressed oxygen requirements.

The above summary is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

It will be appreciated that the exemplary systems and methods shown in the drawings are not necessarily drawn to scale, with emphasis instead being placed on illustrating the various aspects and features of the illustrated embodiments. The drawings illustrate exemplary embodiments, in which.

DETAILED DESCRIPTION OF THE EXEMPLARY EMBODIMENTS

Figure 1:
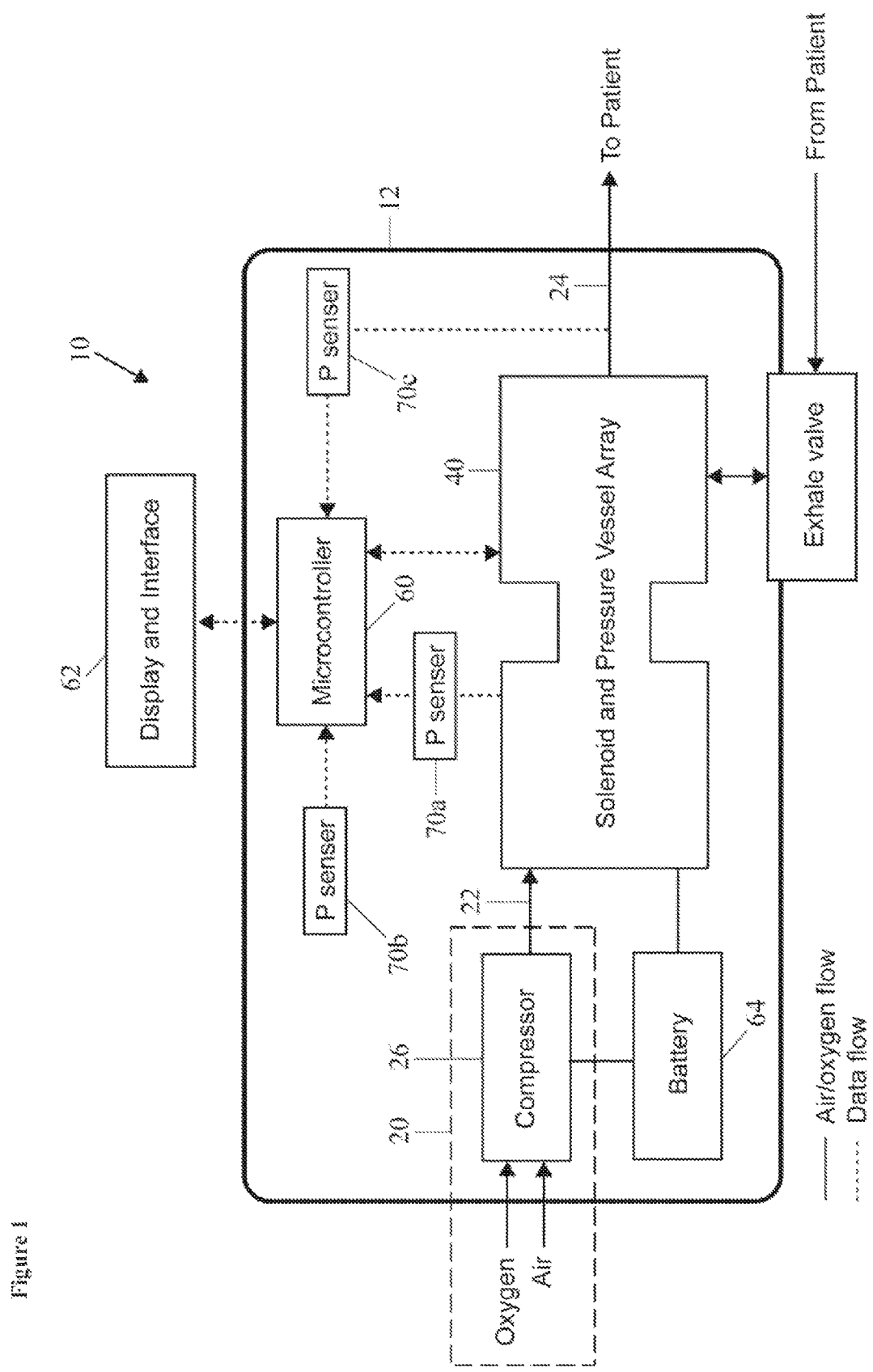
FIG. 1 is a general schematic of an exemplary embodiment of a ventilator indicating air and data flow paths between components of the ventilator.
Figure 2:
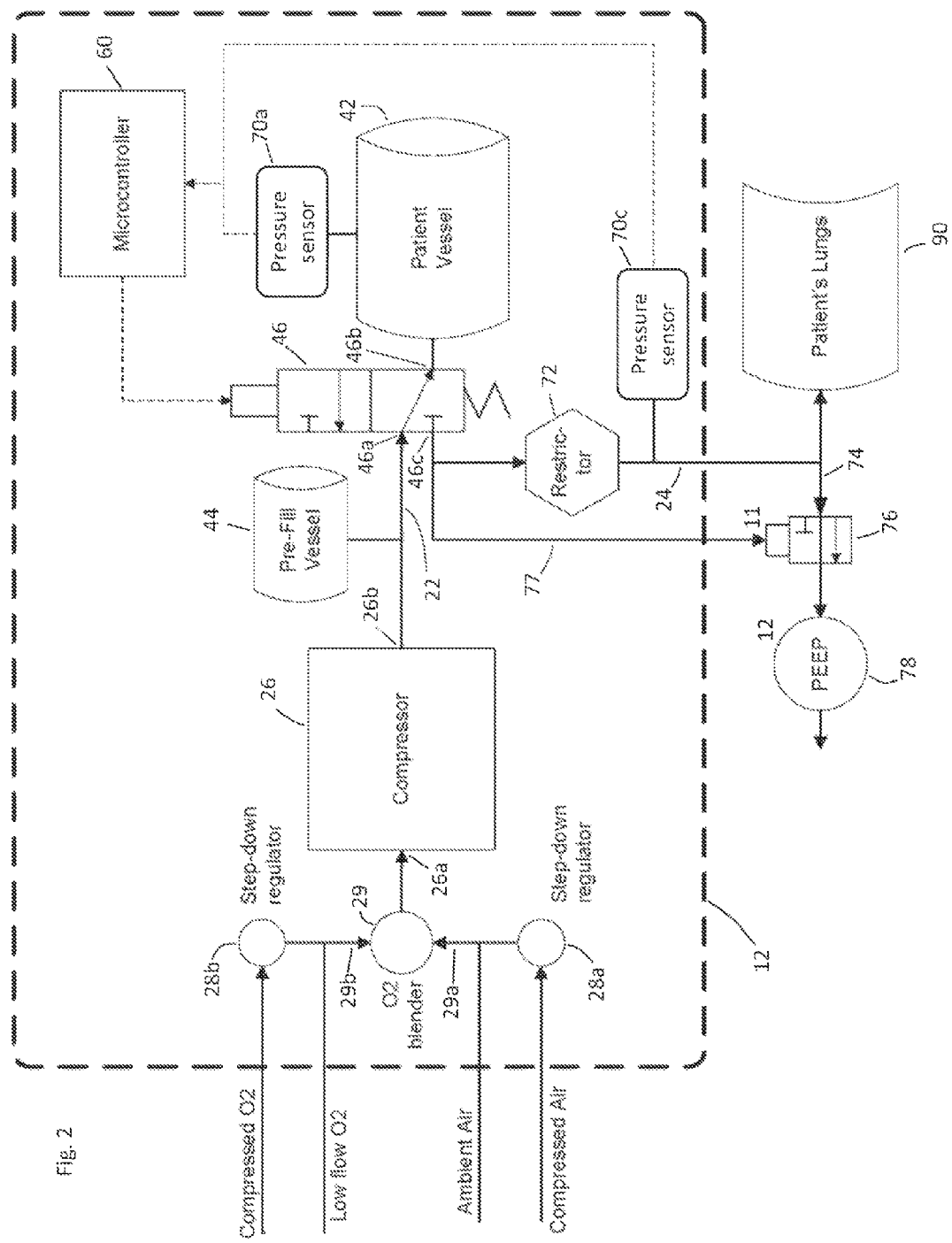
FIG. 2 is a detailed schematic of the ventilator of FIG. 1 showing an exemplary arrangement of gas flow and control components of the ventilator.

Turning to the drawings, FIG. 1 shows an exemplary embodiment of a ventilator system 10, e.g., a portable ventilator that includes a relatively light-weight housing 12 carrying various components of the system 10. Generally, the system 10 includes one or more source lines 22 that receive gas from one or more sources of pressurized gas 20 and an array 40 including one or more storage vessels and/or valves communicating with the gas source(s) 20 via the source line(s) 22 and/or communicating with an inhalation line 24, e.g., for delivering gas to a patient, as described further below. For example, as shown in FIG. 2, the array 40 may include a valve assembly 46 including one or more valves communicating with one or more storage vessels 42. The system 10 may also include one or more controllers 60 coupled to the array 40, e.g., for operating one or more valves of the array 40, to one or more sensors, e.g., pressure sensors 70 that provide pressure data from one or more components of the system 10, and/or to other components of the system 10.

Optionally, the system 10 may also include one or more additional components, e.g., one or more user interfaces 62, power sources 64, flow restrictors 72, valves 76, 78, filters, and the like, carried by the housing 12, as described further below. In addition or alternatively, the system 10 may include one or more external components, e.g., sources of pressurized gas and/or fluids, power sources, tubing, valves, and the like (not shown), and the housing 12 may include various connectors, e.g., pneumatic or electrical connectors (also not shown), for coupling such components to the system 10.

Generally, the ventilation system 10 may controllably deliver gas to a patient via the inhalation line 24 and external tubing and/or other components coupled to the inhalation line 24, e.g., an endotracheal tube (not shown). The ventilation system 10 may control the flow rate and/or volume of the gas delivered to the patient, and/or may control the resistance against the exhalation from the patient, e.g., as described further below. It will be appreciated that the terms "gas" or "air" may be used generically herein, even though the particular fluid involved may be air, oxygen, and the like whether under positive gauge pressure ("pressurized") or substantially zero gauge pressure ("ambient"), and/or may include other fluids, such as anesthetics, nitrous oxide, carbon dioxide, and the like.

With additional reference to FIG. 2, an exemplary configuration of a source of pressurized gas 20 is shown that includes an air compressor 26, one or more step-down orifices or other restrictors 28, an optional pre-fill vessel 44, and an optional oxygen control valve 29 for controlling delivery of external pressurized gas into the system 10. The components of the gas source 20 and/or other components communicating along gas flow paths may be coupled by one or more flow paths, e.g., including tubing or other conduits, manifolds, and the like (not shown), as desired.

The compressor 26 may be any device capable of drawing ambient air or other gas into the system 10 and compressing the gas to one or more desired pressures for delivery to the source line 22. The compressor 26 generally includes one or more inlets, e.g., an inlet 26a communicating with the control valve 29 for drawing gas into the compressor 26, and an outlet 26b doe providing pressurized gas to the source line 22. Alternatively, the compressor 26 may include a plurality of inlets (not shown), e.g., an inlet for drawing ambient air into the compressor and an inlet for receiving gas from the oxygen control valve 29 or other external source. If the compressor 26 draws ambient air from an area outside the housing 12, one or more filters (not shown) may be provided upstream of the compressor inlet 26a, if desired, to remove dust or other debris. In exemplary embodiments, the compressor 26 may be capable of delivering pressures equal to or greater than about 700 cm $H_2O$ (10 psi), or equal to or greater than about 350 cm $H_2O$ (5 psi).

The oxygen control valve 29 may be coupled to one or more external sources of gas, such as a fixed volume source, e.g., a cylinder or tank, a substantially continuous source, e.g., an air or oxygen supply line from a hospital or other health care facility, a concentrator, an external pump or compressor, and the like (not shown). Optionally, the oxygen control valve 29 may include a bypass valve or position and a line (not shown) may be provided that bypasses the compressor 20 and instead delivers gas from the external source(s) directly to the source line 22, if desired.

As shown, the oxygen control valve 29 may include two inlets 29a, 29b that may be coupled to different external gas sources. For example, inlet 29a may be coupled to one or more external sources of air, e.g., ambient air and/or compressed air, while inlet 29b may be coupled to one or more external sources of pure oxygen, e.g., low flow oxygen and/or compressed oxygen. Each line communicating with the inlets 29a, 29b of the oxygen control valve 29 may include a step-down regulator 28a, 28b, e.g., if the external source(s) including compressed gas, to ensure that a maximum predetermined pressure is not exceeded. The housing 12 may include connectors (not shown) for coupling the external source(s) to the system 10 for delivery into the oxygen control valve 29 and compressor 26.

The oxygen control valve 29 may control a ratio or mixture of the gases from the external sources communicating with the inlets 29a, 29b that is delivered to the compressor 26. For example, the oxygen control valve 29 may be a multiple position device, e.g., a two-, three- or four-position regulator or control valve, which may be manually actuated by a user or electronically actuated by the controller 60. For example, the oxygen control valve 29 may have discrete settings to deliver about twenty one percent (21%) (i.e., no supplemental oxygen), about fifty percent (50%), or about one hundred percent (100%) oxygen to the compressor inlet 26a (or directly to the source line 22) from the external sources (not shown). At the about one hundred percent (100%) setting of the oxygen control valve 29, substantially the only gas delivered to the patient is from the external oxygen supply. Thus, the oxygen control valve 29 may be adjusted to control the rate of oxygen released (e.g., as calculated as a ratio of oxygen volume to air volume). Alternatively, the control valve 29 may be omitted and any external gas source may be coupled to the compressor 26 and/or source line 22 simply via a connector on the housing 12.

Optionally, a step-down restrictor (not shown) may be provided in the source line 22. For example, the restrictor may be may be an orifice or other device that regulates gas entering the valve assembly 46, e.g., to ensure that a maximum pressure is not exceeded regardless of the source, i.e., whether the gas is from the compressor 26 or an external source via the control valve 29. For example, such a pressure step-down restrictor may limit the pressure delivered to the valve assembly 46 from the source line 22, i.e., from the compressor 26 and/or control valve 29, e.g., to not more than about 700 cm $H_2O$ (10 psi).

If desired, the gas source 20 may include one or more vessels or reservoirs for temporarily storing gas delivered from the compressor 26 and/or external source(s). For example, as shown in FIG. 2, a pre-fill vessel 44 may be provided that communicates with the source line 22 such that pressurized gas from the compressor 26 may be delivered into the pre-fill vessel 44 and/or stored gas in the pre-fill vessel 44 may be delivered into the source line 22, e.g., to supplement gas delivered to the valve assembly 46 and/or patient vessel 42, as described further below.

The compressor 26 and/or other components may be powered by one or more power sources, e.g., one or more batteries. For example, a single array of rechargeable batteries 64 may be provided within the housing 12 (shown in FIG. 1) that may be coupled to all of the components of the system 10 requiring electrical power. Alternatively, separate power sources (not shown) may be provided for the compressor 26, the controller 60, and/or the valves of the array 40, if desired.

In addition or alternatively, the power source may include a connector (not shown) for coupling the system 10 to an external power source, such as a generator, one or more power cells, batteries, a wall outlet from a building, and the like (not shown). If the external power source is an AC source, the system 10 may include a DC adapter (not shown), e.g., within or external to the housing 12, for converting the power for use by components of the system 10. Optionally, when an external power source is connected to the system 10, the system 10 may selectively or automatically recharge the one or more batteries.

Optionally, the ventilation system 10 may include a CPAP or BiPAP circuit (not shown), which may bypass the valve assembly 46 and provide an alternative flow path between the source line 22 and the inhalation line 24. For example, a manual or automatic switch (not shown), e.g., controlled by the user and/or the controller 60 may open the BiPAP circuit, preventing gas from entering the valve assembly 46. The CPAP circuit may include a line that communicates directly from the source line 22 to the inhalation line 24 to deliver a substantially continuous stream of pressurized air or other gas to a patient at a predetermined pressure. Alternatively, a BiPAP circuit may deliver a substantially continuous stream of pressurized gas at two or variable pressures. The CPAP or BiPAP circuit may include a fixed or variable flow restrictor for delivering a substantially continuous stream of pressurized gas to a patient at one or more predetermined pressures. The controller 60 may be coupled to a BiPAP or CPAP switch (not shown) in the circuit, and, when operating in BiPAP or CPAP mode, the controller 60 may adjust the BiPAP or CPAP switch to route the pressurized gas from the gas source 20 through the BiPAP or CPAP circuit, bypassing the valve assembly 40.

With particular reference to FIG. 2, the system 10 generally includes one or more storage vessels or reservoirs, e.g., a patient storage vessel 42, for storing pressurized gas, and the valve assembly 46 includes one or more valves for directing flow of pressurized gas between the patient vessel(s) 42, the supply line 22, and/or the inhalation line 24. In the exemplary embodiment shown, the valve assembly 46 may include a single valve, e.g., a three-port, two-position solenoid valve, such as an electromechanical solenoid valve assembly, hydraulic valve assembly, pneumatic valve assembly, and the like.

For example, as shown, the solenoid valve assembly 46 may have an incoming port 46a coupled to the source line 22, a port 46b from the solenoid valve assembly 46 for communicating with the one or more storage vessels 42, and an outgoing port 46c to the inhalation line 24. Thus, the solenoid valve assembly 46 may control the gas flow from the gas source 20 and source line 22 to the patient vessel 42 and from the patient vessel 42 to the inhalation line 24, as described further below.

Alternatively, the valve assembly 46 may include two or more valves that may open or close selected flow paths through the ventilator 10, e.g., a first flow path between the source line 22 and the patient vessel 42, and a second flow path between the patient vessel 42 and the inhalation line 24, as described further below. Thus, in either embodiment, the valve assembly 46 may be directed between two or more configurations, for example, between a storage configuration and a delivery configuration, as described further below. In the delivery configuration, a first flow path may be opened between the patient vessel 42 and the inhalation line 24, e.g., for delivering ventilation gas from the patient vessel 42 to a patient, while in the storage configuration, a flow path may be formed between the gas source 20 and the patient vessel 42, e.g., for delivering pressurized gas into the patient vessel 42 to recharge or refill the patient vessel 42, as described further below.

Generally, the patient vessel 42 may be sized to approximate a maximum expected single tidal volume, i.e., a single bolus of gas delivered to a patient during a single inhalation, at an expected maximum vessel pressure. For example, the patient vessel 42 may hold up to about two thousand cubic centimeters (2,000 cc) of gas at about 56 cm $H_2O$ in the vessel to deliver a 800 cc tidal breath at about 40 cm $H_2O$ in a patient, or up to about four hundred cubic centimeters (400 cc) of gas at about 60 cm $H_2O$ in the vessel to deliver a 800 cc tidal breath at 20 cm $H_2O$ in a patient. Vessel volume and maximum pressure may also vary based on resistance to gas flow in the ventilator or patient circuit. As an example, a relatively higher pressure or larger vessel may be desired to increase the flow of gas to the patient. Thus, the patient vessel 42 may be a substantially rigid cylinder or other enclosed reservoir having a volume between about four hundred and two thousand cubic centimeters (400-2000 cc).

Alternatively, the system 10 includes two pressure vessels, for example, a large patient pressure vessel and a small patient pressure vessel (not shown), e.g., as described in provisional application Ser. No. 61/260,296. If the system 10 includes multiple pressure vessels, the pressure vessels may be structurally identical in size and/or shape or may have different sizes and shapes. In this alternative, the valve assembly 40 may include one or more pressure vessel switches (not shown) that may be in data communication with and/or under the control of the controller 60, e.g., for controlling flow between the vessels and/or the other lines of the system 10. For example, when actuated, e.g., by the controller 60, the pressure vessel switch(es) may route gas flow between the patient vessels to or from the valve assembly 46, and/or to or from either or both pressure vessels, e.g., as described in application Ser. No. 61/260, 296.

The patient vessel 42 may include one or more pressure sensors, such as patient vessel pressure sensor 70a. Optionally, if the system 10 includes a pediatric (or other additional) storage vessel (not shown), the pediatric storage vessel may also include one or more pressure sensors, such as a pediatric storage vessel pressure sensor (also not shown). The storage vessel pressure sensor(s) 70a may be located inside or adjacent to, but communicating with, the internal volume of the patient vessel 42. The pressure sensor(s) 70a may be coupled to the controller 60, e.g., for providing pressure data for the patient vessel 42 to the controller 60, as described further below.

Optionally, the system 10 may include one or more additional pressure sensors, which may be coupled to the controller 60 for providing pressure data that may be used by the controller 60 during operation of the system 10. For example, the system 10 may include an atmospheric pressure sensor 70b, which may be exposed to external ambient pressure to provide atmospheric pressure data to the controller 60.

In addition, a patient airway sensor 70c may be provided in the inhalation line 24, e.g., to detect the pressure in the inhalation line 24 where the inhalation line 24 communicates with the patient's airway, as described further below.

In addition, the ventilation system 10 may include one or more regulators and/or valves, e.g., in the inhalation line 24 and/or an exhalation line 74 of the system 10. For example, a flow restrictor 72 may be provided in the inhalation line 24, e.g., between the patient 90 and the valve assembly 46. The flow restrictor 72 may be configured to limit the inspiratory pressure delivered to the patient, e.g., to a maximum of about 60 cm $H_2O$ (0.9 psi). Optionally, the flow restrictor 72 may be adjustable for controlling the flow rate of ventilation gas delivered to the patient during inhalation. For example, the flow restrictor 72 may be manually adjustable for changing a maximum flow rate deliverable through the inhalation line 24 to the patient 90, e.g., such that the flow restrictor 72 is decoupled from the controller 60. For example, the flow restrictor 72 may be adjustable via a knob or other control (not shown) on the housing 12 or by directly accessing the flow restrictor 72. Alternatively, if desired, the flow restrictor 72 may be coupled to the controller 60, e.g., such that the controller 60 may actuate the flow restrictor 72 to adjust the maximum flow rate based upon user input and/or based on operating parameters of the system 10.

Optionally, the ventilation system 10 may include a pressure relief valve (not shown), e.g., also in the inhalation line 24 downstream of the flow restrictor 72 and the patient 90. The pressure relief valve may be configured to automatically open and release excess pressure that may occur in the inhalation line 24, e.g., to limit the inspiratory pressure to a pressure of not more than about 60 cm $H_2O$ (0.9 psi).

The patient airway sensor 70c may be provided in the inhalation line 24 downstream of the flow restrictor 72 and/or pressure relief valve, e.g., adjacent a connection point to a patient circuit outside of the housing 12. The controller 60 may be coupled to the patient airway sensor 70c to detect the inhalation pressure to which the patient is exposed. For example, the controller 60 may use data from the patient airway sensor 70c to determine peak airway pressure, static and/or dynamic airway pressure, and/or other parameters.

A separate pressure sensor 70b is used to measure atmospheric pressure. The atmospheric pressure sensor 70b returns data to the controller 60 used in determining patient breath triggering (−2 to −5 cm H2O change) in conjunction with data from the airway pressure sensor 70c. As described further below, calibration routine may be performed with each new patient. During the calibration process, the patient circuit is connected and capped, and the controller 60 may cycle ventilation gas air though the circuit and record the volume, which is subtracted from the displayed tidal volume to provide a closer estimation of physiologic tidal volume.

In addition, the ventilation system 10 may have an expiratory block, e.g., external to the housing 12, through which the patient may exhale. For example, as shown in FIG. 2, the expiratory block may include an exhale valve 76 and a PEEP ("positive end expiratory pressure") valve 78, which may be connected to external tubing communicating with the inhalation line 24. Either or both of these valves 76, 78 may be removable, disposable and/or washable for reuse, or permanently attached to the tubing, the housing, or other component of the system 10.

The exhale valve 76 may be configured to open to the atmosphere during exhalation and close during inhalation. An exhale gas line 77 may communicate from the valve assembly 46 to the exhale valve 76, e.g., and optionally, a valve, e.g., a two-port solenoid valve (not shown) may be provided in the exhale valve gas line 77 for controlling air flow into the exhale valve gas line 77. The exhale valve 76 may route exhalation from the patient 90 between the PEEP valve 78 and an optional release valve, e.g., a substantially zero-resistance release solenoid valve (not shown). The release valve may be coupled to the controller 60 and/or a power source (not shown), which may be selectively opened and closed. For example, when the release valve is opened, the exhale valve 76 may route exhalation gas out of the open release valve. When the release valve is closed, the exhale valve 76 may route exhalation gas to the PEEP valve 78. The release valve may be integral with the exhale valve 76, or may be a separate, attached component from the exhale valve 76.

The PEEP valve 78 may be automatically and/or manually adjustable to set a desired PEEP pressure and/or may be a spring-loaded valve. For example, the PEEP valve 78 may be coupled to the controller 60, which may actuate a motor or solenoid (not shown) within the PEEP valve 78 to adjust the PEEP pressure. The PEEP pressure may be, for example, between about 0 $H_2O$ (0 psi) and about 30 cm $H_2O$.

As described above, the controller 60 may be coupled to the various components of the system 10, e.g., for receiving data and/or controlling operation of various components of the system 10. The controller 60 may include one or more hardware components, e.g., one or more processors, memory, storage devices, and the like (not shown) and/or software modules that control one or more aspects of the operation of the apparatus 10. The controller 60 may be coupled to the user interface 62, which may include one or more displays, input devices, and the like, to display operating parameters and/or other information regarding the system 10 and/or to allow a user to set parameters or otherwise provide input into the operation of the system 10.

For example, the controller 60 may be coupled to receive pressure data from the patient vessel pressure sensor 70a, the atmospheric pressure sensor 70b, the patient airway sensor 70c, and/or other pressure sensors (not shown) of the ventilation system 10 and display one or more parameters and/or operate the system 10 based at least in part on the pressure data obtained. The controller 60 may send and/or receive control data to and from the valve assembly 46, BiPAP switch, release solenoid valve, and/or other operable components of the system 10.

Using the data from the patient vessel pressure sensor 70a, the controller 60 may determine the tidal volume and minute volume based at least in part on the pressure drop from the beginning of inhalation. For example, the controller 60 may sense the beginning of the patient's breath when a predetermined change in pressure is detected, e.g., about a −2 cm $H_2O$ (0.03 psi) change within 0.01 sec to 0.5 sec, more narrowly 0.1 sec to 0.3 sec, for example, about 0.2 sec based on pressure data from the patient airway sensor 70c.

The user may set performance characteristics of the ventilation system 10 via the user interface 60 to the controller 60. For example, the user may set the inspiratory pressure, oxygen concentration, inhalation to exhalation ratio, PEEP pressure, or combinations thereof.

The controller 60 may control the mode of ventilation, for example, by controlling the valve assembly 46, the BiPAP switch, and/or other components of the system 10. For example, the controller 60 may be used to set the ventilation system 10 to operate in one or more modes, such as control mode ventilation ("CMV"), Assist-Control ("A-C" or "A/C") mode ventilation, or BiPAP or CPAP mode ventilation, as described elsewhere herein.

In control mode ventilation, the ventilation system 10 may deliver individual, discrete, pressurized volumes of air ("ventilator breaths") to the patient at a substantially fixed rate. The inhalation-to-exhalation ratio may be, for example, 2:1, 1:1, 1:2, 1:3, or 1:4. The inspiratory rate may be, for example, between about zero and sixty (0-60) breaths per minute. The ventilation system 10 may be controllable to adjust breaths per minute in increments, e.g., of one breath per minute.

In assist-control mode ventilation, the patient may initiate inhalation (e.g., when the patient inhalation generates a −2 cm $H_2O$ (0.03 psi) change in the pressure sensed through the patient pressure sensor). The controller 60 may then control the valve assembly 46 to route ventilation gas from the patient vessel 42 to flow into the inhalation line 24 and/or flow restrictor 72. If a patient inhalation is not detected in a given amount of time, from about two seconds (2 sec) to about eight seconds (8 sec), e.g., about six seconds (6 sec), the controller may trigger a ventilator breath. The user may adjust a rescue breath timer, e.g., via the user interface 62, to set the time before the controller 60 triggers a ventilation breath.

In BiPAP or CPAP mode, the controller 60 may adjust the BiPAP (or CPAP) switch to route pressurized gas from the source line 22 through the BiPAP (or CPAP) circuit, bypassing the valve assembly 46, to deliver substantially continuous gas pressure to the patient.

The system 10 also be configured to operate in a Synchronized Intermittent Mechanical Ventilation ("SIMV") mode and a Pressure Supported SIMV ("PS-SIMV") mode. As a patient recovers from respiratory distress, the patient may be weaned from mechanical ventilation back to spontaneous breathing. The weaning may be accomplished using a patient-triggered synchronized mode of ventilation, for example, synchronized intermittent mandatory ventilation (SIMV) mode or assist control mode.

SIMV provides a preset number of mechanical breaths synchronized with the patient's spontaneous and unassisted efforts. In PS-SIMV mode, each patient-initiated breath is supported with a pre-set amount of pressure chosen by the operator.

In SIMV mode, the ventilation system 10 may use the same inhale triggering algorithm used in A/C mode to sense spontaneous inhalation. However, this breath is not supported with positive pressure from the system 10. Instead, the exhale valve 76 is opened when the SIMV mode is chosen and the patient inhales ambient air plus PEEP, performing all the work of breathing themselves. The exhale valve 76 may remain open during SIMV mode except during the inhale cycle of a ventilator breath.

Generally, with additional reference to FIG. 2, during operation, the flow of air through the system 10 may be described as follows. Pressurized gas may be provided to the source line 12, e.g., supplied from the compressor 22 and/or one or more external sources (not shown), as described above. The pressurized gas from the source line 22 may be delivered to the valve assembly 46, which may control flow to the patient vessel 42 and/or inhalation line 24. For example, during a storage phase, the valve assembly 46 may be directed to a storage configuration that opens a flow path from the source line 22 to the patient vessel 42. Thus, pressurized gas may be delivered into the patient vessel 42 to recharge or refill the patient vessel 42. During a delivery phase, the valve assembly 46 may be directed to a delivery configuration that opens a flow path from the patient vessel 42 to the inhalation line 24. Thus, ventilation gas from the patient vessel 42 may be delivered to a patient via the inhalation line 24 with the patient vessel 42 and inhalation line 24 isolated from the source line 22.

If the system 10 includes a pre-fill vessel 44, the pre-fill vessel 44 may remain in constant communication with the source line 22. For example, during the delivery phase, the pre-fill vessel 44 may receive pressurized gas from the compressor 26 or external sources, while during the storage phase, the pre-fill vessel 44 may supplement pressurized gas delivered to the patient vessel 42.

The pressure sensor 70a coupled to the patient vessel 42 provides pressure data to the controller 60, which uses the data to determine tidal volume and/or minute ventilation based at least in part or solely on the pressure drop from the beginning to end of an inhalation.

The flow restrictor 72 limits or controls the flow rate of ventilation gas delivered to the patient via the inhalation line 24 during inhalation. Downstream of the flow restrictor 72, ventilation gas passes the pressure relief valve, e.g., set to open at about 60 cm H2O, and the patient airway sensor 70c, e.g., located at the connection point to the external patient circuit. The patient airway sensor 70c returns data to the controller 60, which may use the data to determine peak airway pressure, which may be displayed on a control panel of the user interface 62. Air exhaled by the patient is returned through the exhale valve 76, which is open to the atmosphere during exhalation and held closed during inhalation. The exhale gas line valve (not shown), which may be powered by the same or different power source as other components of the system 10, controls air flow into the exhale valve gas line 77. Before exiting the device, exhaled air passes through the positive end expiratory (PEEP) valve 78.

The atmospheric pressure sensor 70b is used to measure atmospheric pressure. The controller 60 uses data from the sensor 70b, e.g., in determining patient breath triggering (−2 to −5 cm H2O change) in conjunction with data from the patient airway sensor 70c.

Before use of the system 10, a calibration routine may be performed with each new patient. During the calibration process, the external patient circuit is connected to the inhalation line 24 and capped. The system 10 is then operated to cycle ventilation gas through the circuit and the controller 60 records the measured volume, which is subtracted from the displayed tidal volume to provide a closer estimation of physiologic tidal volume.

Figure 3A:
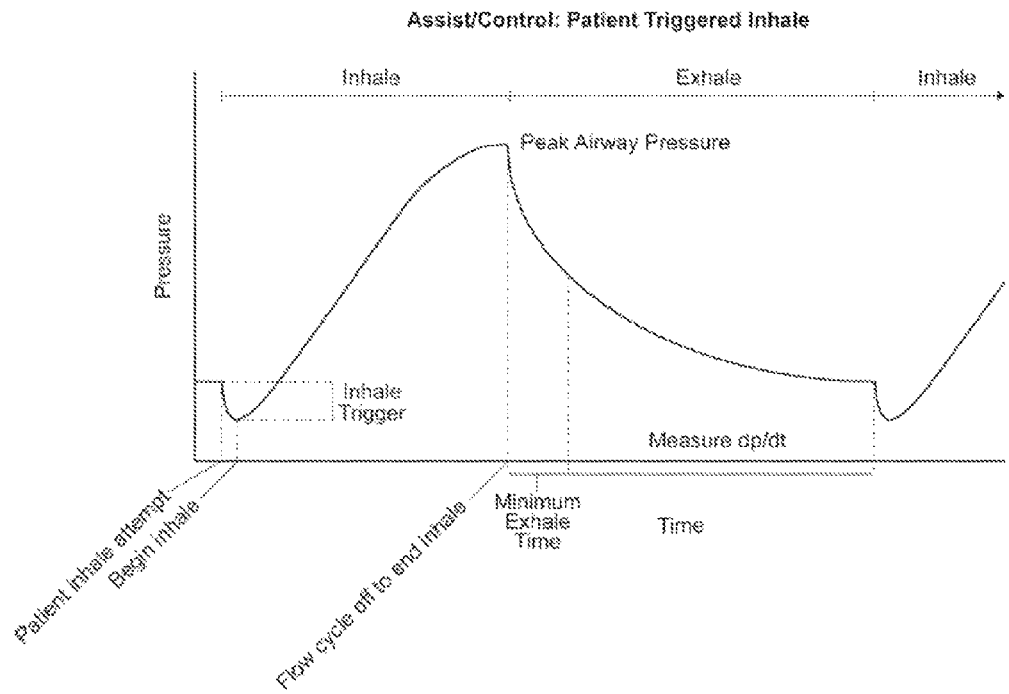
FIGS. 3A and 3B are time-synchronized graphs of patent airway pressure cycling and pressure vessel pressure cycling, respectively, during an exemplary method for operating a ventilation system, such as the ventilator of FIGS. 1 and 2.
Figure 3B:
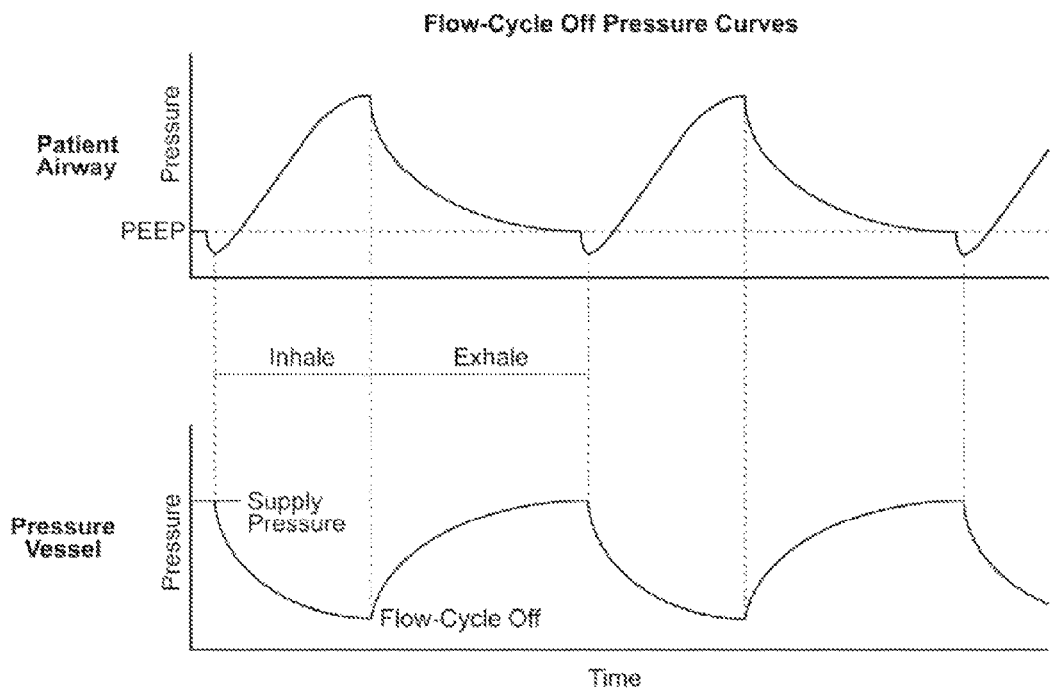

FIGS. 3A and 3B illustrate pressure parameters of the system 10 when operated in Assist/Control mode ventilation. As shown in FIG. 3A (with additional reference to FIG. 2), a patient inhale attempt at point A may trigger air delivery from the system 10 when a predetermined drop in pressure is detected at the patient airway sensor 70c. Depending on the mode selected, either a specified pressure, inhale time, or volume limit may signal the controller 60 to adjust the valve assembly 46 to stop airflow through the inhalation line 24 to the patient. For example, if the controller 60 is set to discontinue delivery at a predetermined peak pressure, pressure limits are detected by the patient airway sensor 70, while if the controller is set to discontinue delivery at a predetermined volume limit, tidal volumes are detected by the patient vessel pressure sensor 70a. Optionally, the controller 60 may track time of inhale and exhale and atmospheric pressure.

To suppress false triggering (auto-cycling), the controller 60 may wait for a predetermined minimum exhale time before it analyzes the exhalation pressure. For example, as shown in FIG. 3A, after the minimum exhale time passes at point D, the controller 60 may analyze the change in pressure over time, measuring dp/dt, to determine the inhalation trigger when dp/dt exceeds, for example, about −2 cm H2O per 0.1 sec. At that time, the pressure cycle starts over.

FIG. 3B compares the changes in pressure between the patient airway and the patient vessel over time. As described above with reference to FIG. 3A, at point A, a patient may attempt to inhale, which may trigger the controller 60 to direct the valve assembly 46 to the delivery configuration at point B. As shown, at point B, the pressure within the patient vessel 42 may be maximized immediately before the valve assembly 46 is directed to the delivery configuration to open a flow path between the patient vessel 42 and the inhalation line. During inhalation, after point B, pressure within the patient airway increases and pressure within the patient vessel 42 decreases.

At point C, the controller 60 directs the valve assembly 46 to the storage configuration, closing the flow path between the patient vessel 42 and the inhalation line 24 and opening a flow path between the patient vessel 42 and the source line 22, thus discontinuing delivery of ventilation gas to the patient. Consequently, pressure within the patient airway begins to decrease. With the patient source vessel 42 communicating with the gas source 20, e.g., the compressor 26, external source(s), and/or pre-fill vessel 44, via the source line 22, pressure within the patient vessel 42 increases between points C and E, as shown.

Figure 4:
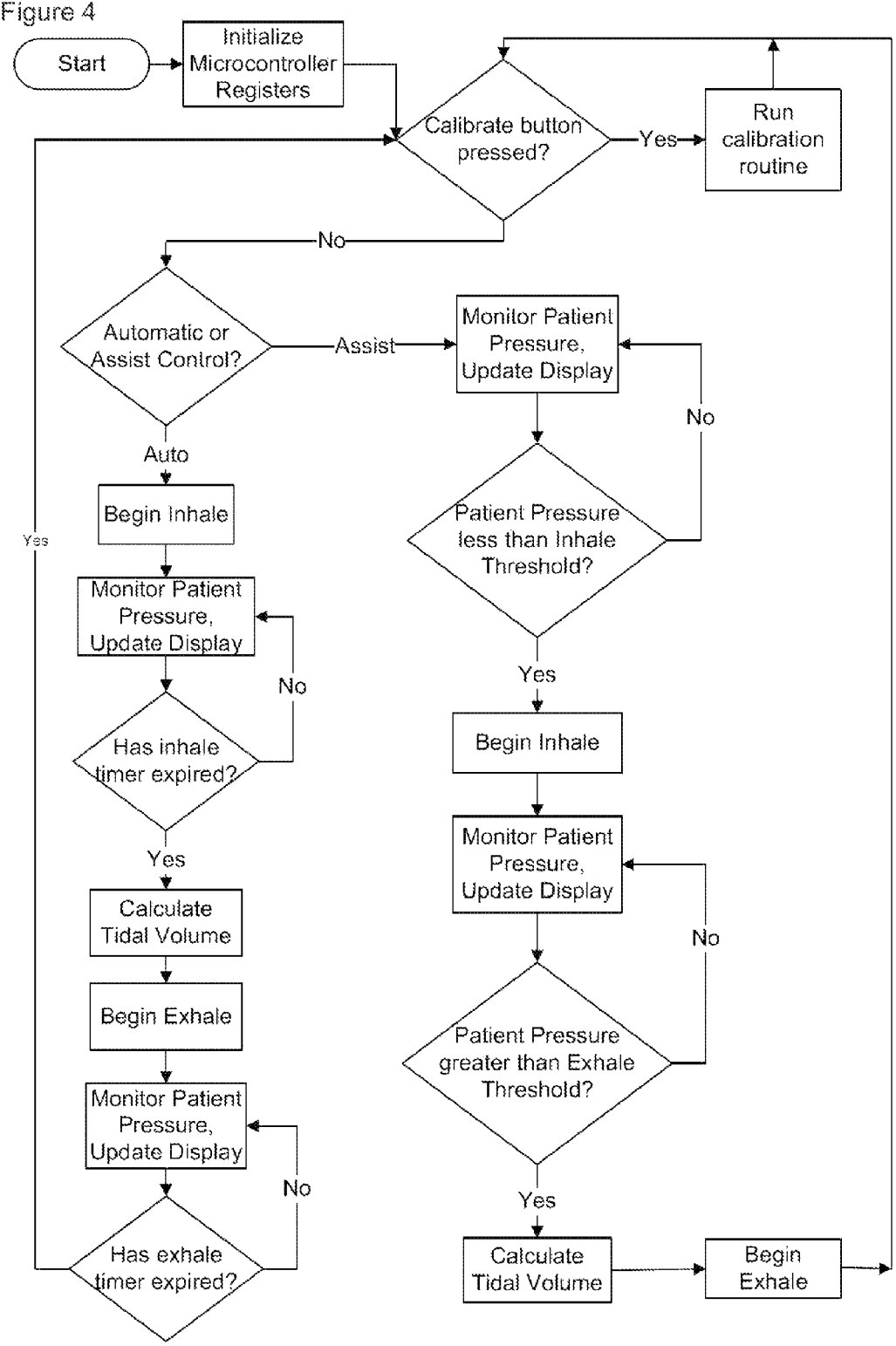
FIG. 4 is a flowchart showing exemplary algorithms for operating a ventilator, such as the ventilator of FIGS. 1 and 2.

FIG. 4 illustrates an exemplary algorithm or instructions the controller 60 may execute during operation of the system, e.g., including an inhalation trigger algorithm that may be initiated beginning at exhalation of a patient placed on the system 10. As described above, the controller 60 may include one or more processors, memory, and other hardware components, and/or one or more software modules for performing the various functions of the controller 60. For example, in one embodiment, the controller 60 may include a single electrical circuit board that includes a plurality of electrical components thereon for operating the system 10. Alternatively, the controller 60 may be provided as multiple subcontrollers that control different aspects of the operation of the system 10.

At step 110, the system 10 may be initialized, e.g., when an "on" switch or other input has been activated from the user interface 62 to turn the system 10 on. Any registers of the controller 60 may be initialized at this time, and/or any hardware components of the system 10 may be tested and/or activated. For example, the controller 60 may store one or more parameters in memory (not shown), e.g., a "minimum slope" value for the derivative of pressure over time in the patient airway during exhalation of the controller 60, and/or a value for PEEP, for subsequent operation, which may be fixed or may change during operation. In an exemplary embodiment, when the algorithm begins, the controller 60 may reset the value for PEEP in the controller memory to zero (0).

At step 112, the controller 60 may poll the input device(s) of the user interface 62, e.g., to determine whether the user has instructed the controller 60 to calibrate the system 10. For example, the user interface 62 may include a fixed calibrate button 62a (see FIG. 5A) or calibration may be selected from a set of menus, e.g., on a touch screen or other input device. If the controller 60 determines that calibration should be performed, the controller 60 may execute a calibration at step 114.

The total volume of air delivered by a ventilator during a single inhalation is made up of two components: "tidal volume," the air actually filling the patient's lung, and dead space. Dead space may include the patient's airway from the mouth to the lungs, called "physiologic dead space," which includes the trachea and major bronchi, and the volume of the "patient circuit," i.e., the flow path connecting the patient to the ventilator. The calibration procedure may involve determining the volume of air in the patient circuit at a given inspiratory pressure. This volume may later be subtracted from the total volume delivered from the patient vessel 42 during an inhalation and displayed as tidal volume. Calibrating the system 10 to get a more accurate tidal volume excluding the dead space may be used for all patients, for example, for pediatric or small patients, where tidal volumes may be equal to or less than the patient circuit volume.

During calibration, the system 10 may deliver a single breath or a set number of breaths, for example, five breaths, at an inspiratory pressure set by the operator. The inspiratory pressure chosen to perform the calibration procedure should be the same or similar to the inspiratory pressure applied during patient use. During the calibration procedure, the patient circuit is attached to the system 10 but the end is capped, for example, with a plastic cap or the operator's thumb. The volume delivered from the patient vessel 42 is recorded for each of the breaths delivered during the calibration procedure. The average of these volumes may be determined and stored in memory of the controller 60, whereupon the calibration procedure is finished. The stored average patient circuit volume is subtracted from every tidal volume during subsequent delivery of ventilation gas, and the difference may be displayed on the user interface 62 and/or stored in memory of the controller 60. The average patient circuit volume may remain in memory and/or be used by the controller 60 until the calibration procedure is repeated or the system 10 is turned off. The calibration procedure may be repeated at any time, provided the patient circuit is disconnected from a patient.

Figure 5A:
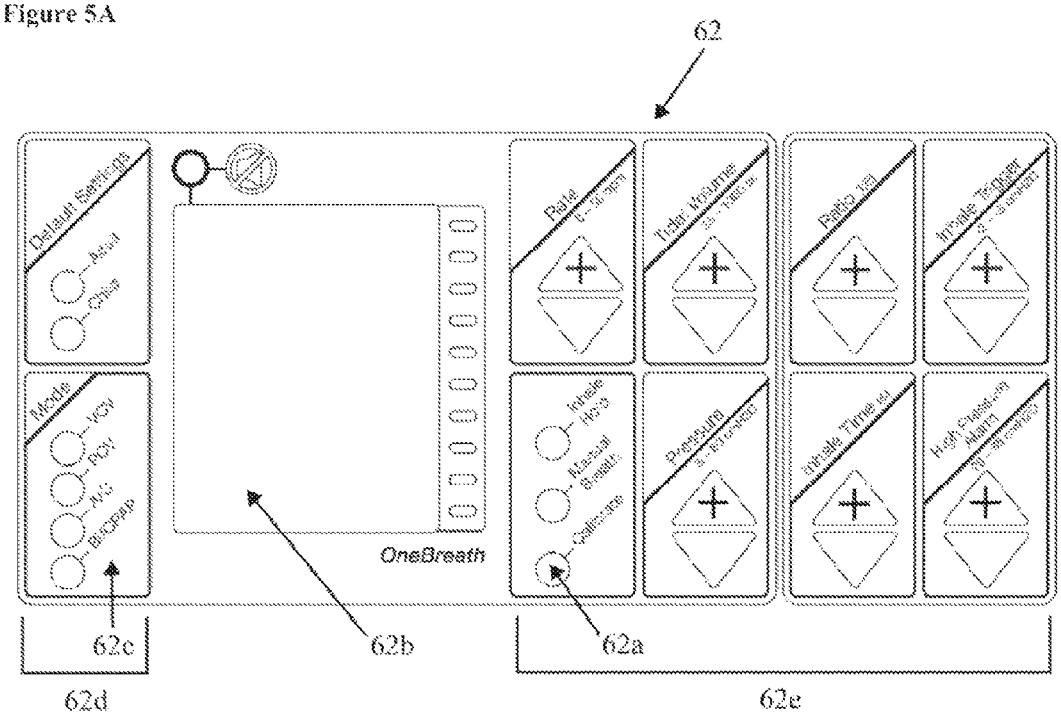
FIG. 5A is a front view of an exemplary user interface panel that may be provided on a housing of a ventilator, such as the ventilator of FIGS. 1 and 2.

Next, at step 120, the controller 60 may poll the user interface 62 to determine whether a particular mode of ventilation has been selected by a user. For example, as shown in FIG. 5A, the user interface 62 may include a menu of modes 62c that may be selected by a user. Returning to FIG. 4, exemplary choices of automatic or assist modes are shown, although it will be appreciated that the controller 60 and system 10 may be operated in more than other modes than these two, such as those described elsewhere herein.

For example, if automatic mode is selected (or no other mode is selected and automatic mode is the default), at step 130, the system 10 may begin inhale, i.e., direct the valve assembly 46 to the delivery configuration to deliver ventilation gas from the patient vessel 42 to the patient via the inhalation line 24. While ventilation gas is delivered to the patient from the patient vessel 42, pressure within the patient vessel 42 may be monitored periodically by the controller 60 at step 132, e.g., using the patient vessel pressure sensor 70a. At step 134, the controller 60 may inquire whether an inhale timer has expired. If not, the controller 60 may return to step 132 and continue to monitor the pressure within the patient vessel 42 as ventilation gas is further delivered. If the controller 60 determines that the inhale timer has expired, the controller 60 may direct the valve assembly 46 to the storage configuration, discontinuing delivery of ventilation gas to the patient.

At step 136, the controller 60 may then determine the tidal volume of ventilation gas delivered to the patient. The controller 60 may determine the tidal volume based at least in part on the change in pressure within the patient vessel 42. For example, tidal volume may be determined simply by measuring the change in pressure in the pressure vessel during the inhalation cycle, e.g., without requiring flow rate and/or duration of gas delivery. At room temperature, air and oxygen are ideal gasses and the volume of the pressure vessel is fixed. Accordingly, the controller 60 may use the ideal gas law (pV=nRT) to determine the moles of gas dispensed by the pressure vessel during inhalation. The controller 60 may then determine the volume of gas under the patient airway pressure, which equals tidal volume.

The controller 60 may determine the minute volume by dividing the total tidal volume inhaled for the past minute by one minute.

At step 138, the system 10 may begin exhale, and, at step 140, may monitor the patient pressure, e.g., using the patient airway sensor 70c. At step 142, the controller 60 may periodically check if the minimum exhalation time has passed. If not, the controller 60 may return to step 140 and continue to monitor the patient pressure.

Optionally, once the minimum exhalation time has passed, the controller 60 may check if a rescue breath is needed (i.e., if it has been too long since the patient's last inhalation). Whether a rescue breath is needed is determined by checking if a rescue breath timer has elapsed. If the rescue breath timer is elapsed, the controller 60 may initiate an inhalation. If a rescue breath is not needed, the controller 60 may determine whether the patient airway sensor 70c detects a pressure less than the PEEP value in the controller's memory. The controller 60 may then initiate an inhalation.

If the patient airway pressure measured by the patient airway sensor 70c is still above the PEEP value stored in the controller's memory, the controller 60 may then sample a pre-determined number of immediately prior readings, for example, about five samples, from the patient airway sensor 70c sensor and check whether the change in pressure over time is less than the inhalation trigger limit, for example about −2 cm H2O per 0.1 sec.

If the change in pressure over time is not less than the inhalation trigger limit (which is less than or equal to zero), the controller 60 may return to the step of the algorithm to check if the rescue breath timer is elapsed.

If the change in pressure over time is greater than the inhalation trigger limit (which is less than or equal to zero), the controller 60 may then check if the recent change in pressure over time is the closest change in pressure over time to zero recorded for the given exhalation (i.e., whether the slope is flat). If the change in pressure over time is less than the inhalation trigger limit, the controller 60 checks if the recent change in pressure over time is greater than the pre-determined minimum slope value. If the recent change in pressure over time is greater than the minimum slope value and the change in pressure over time most recently recorded is the closest to the zero for the given exhalation, the controller 60 may be prepared to set the current pressure as a new PEEP value in the controller's memory, replacing a previous PEEP value. The controller 60 may also then store the most recent change in pressure over time in the controller's memory as the current "flattest" change in pressure over time.

If the recent change in pressure over time is less than the minimum slope value, or the recent pressure change over time is not the closest to zero for the given inhalation, then the algorithm may return to the step of checking if the rescue breath timer is less than zero.

Returning to FIG. 4, if assist mode is selected during operation of the system 10, steps 150-162 may be performed. For example, at step 150, patient pressure may be periodically monitored until, at step 152, the patient pressure falls below an inhale threshold. When this occurs, at step 154 the system may begin inhale, i.e., the controller 60 may direct the valve assembly 46 to the delivery configuration to begin delivering ventilation gas from the patient vessel 42 to the patient via the inhalation line 24. At step 156, the patient pressure may be periodically monitored during gas delivery to determine whether the patient pressure has reached or exceeded an exhale threshold, at step 158. When the patient pressure has reached or exceeded the exhale threshold, gas delivery may be discontinued, and the tidal volume may be determined, at step 160, similar to the methods described above. At step 162, exhale may begin, and the patient vessel 42 may be recharged from the gas source 20, as described above, and the algorithm may be reset.

Figure 5B:
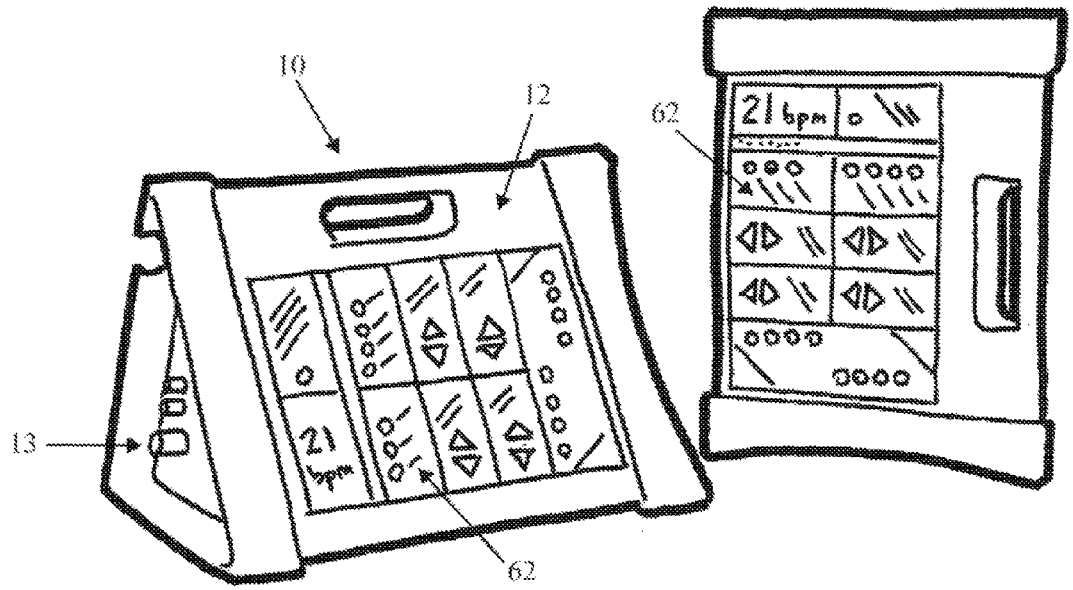
FIG. 5B shows exemplary embodiments of a ventilator system that include a ventilator housing, and a display that is legible in both horizontal and vertical orientations.

FIG. 5A illustrates an example of an intuitive user interface panel 62 that may be provided on a housing of a system, such as those described elsewhere herein. Input controls are grouped according to priority. The most critical functions (breath rate, mode, pressure and volume targets) may be on the user's left, e.g., at 62d, adjacent to a display screen 62b. A default setting button executes a software algorithm to pre-set the device in volume control mode with either an average adult tidal volume and rate, for example, 500 cc and 12 bpm, or an average pediatric tidal volume and rate, for example 200 cc and 14 bpm. Secondary controls for alarm settings and patient inhalation triggering are located further from the display screen, e.g., on the user's right at 62e. In the embodiment shown, text on the control panel 62 is written at a forty five degree (45°) angle to be legible in both upright and horizontal orientations. As illustrated in FIG. 5B, the text on the display screen 62 may be re-oriented by gyroscopic control to appear upright when the ventilation system 10 is in a vertical or horizontal orientation.

FIG. 5B also shows an exemplary embodiment of a housing 12 for a ventilation system 10, such as those described above. As shown, the housing 12 may have a rounded prism shape, e.g., an elongate equilateral triangle shape. The three side surfaces of the housing 12 may be substantially smooth, which may facilitate storage and/or reduce risk of damaging components of the system 10. Optionally, one end of the housing 12 may include a recess in which all connectors 13 for coupling external components, e.g., gas sources, power sources, patient circuit, and the like (not shown), may be located. Thus, the recess may protect the connectors 13 from damage and/or facilitate stacking multiple housings 12 on top of one another with minimal interference from the connectors 13.

In addition or alternatively, if desired, the ends of the housing 12 may include rubber or other absorbable bumpers, e.g., extending around the periphery of the ends to reduce the risk of damage to internal components due to dropping or striking the housing 12. In addition or alternatively, the opposite ends of the housing 12 may have male and female shapes, e.g., to allow a male end of one housing 12 to be nested into the female end of another housing 12, e.g., to facilitate stacking or storage of multiple systems 10.

It is apparent to one skilled in the art that various changes and modifications can be made to this disclosure, and equivalents employed, without departing from the spirit and scope of the invention. Elements shown with any variation are exemplary for the specific variation and can be used on other variations within this disclosure. Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A ventilator comprising:
a housing;
a source of pressurized gas comprising a compressor within the housing for drawing ambient air into the ventilator to provide pressurized air;
a pre-fill vessel within the housing;
a storage vessel within the housing;
a first pressure sensor coupled to the storage vessel for detecting pressure of ventilation gas within the storage vessel;
one or more valves within the housing and communicating with the compressor via a source line, communicating with the pre-fill vessel and the storage vessel, and communicating with an inhalation line for delivering ventilation gas into a patient's airway;
a patient circuit external to the housing and communicating with the inhalation line via tubing configured to deliver the ventilation gas into the patient's airway, the patient circuit comprising an expiratory block including an exhale valve configured to open to the atmosphere during exhalation by the patient and close during inhalation by the patient; and
a controller coupled to the one or more valves for selectively directing the one or more valves between a storage configuration where pressurized air is delivered from the compressor into the pre-fill vessel and the storage vessel, and a delivery configuration where ventilation gas is delivered from the storage vessel into the patient's airway via the inhalation line and pressurized air from the compressor is delivered into the pre-fill vessel,
the controller coupled to the first pressure sensor for detecting a first pressure within the storage vessel when the one or more valves is directed to the delivery configuration, and detecting subsequent pressure thereafter while ventilation gas is delivered from the storage vessel to the patient via the inhalation line, the controller determining a volume of ventilation gas delivered to the patient's airway based at least in part on the difference between the first pressure and the subsequent pressure.

2. The ventilator of claim 1, wherein the controller is configured for detecting subsequent pressure within the storage vessel at predetermined time intervals after directing the one or more valves to the delivery configuration, the controller determining the volume of ventilation gas delivered to the patient based at least in part on a difference between the first pressure and the subsequent pressure.

3. The ventilator of claim 2, wherein the controller compares an estimated cumulative volume of ventilation gas delivered during each time interval to a predetermined maximum volume and directs the one or more valves to close the inhalation line when the estimated cumulative volume meets or exceeds the predetermined maximum volume.

4. The ventilator of claim 1, wherein the first pressure sensor is pneumatically connected to the storage vessel at a location away from any ports in the storage vessel communicating with the one or more valves such that flow through the flow path does not substantially affect the pressure of the pressurized gas detected by the first pressure sensor.

5. The ventilator of claim 1, wherein the controller is configured for determining the volume of ventilation gas delivered to the patient without requiring information regarding a flow rate of the ventilation gas from the storage vessel.

6. The ventilator of claim 1, wherein the controller is configured for determining the volume of ventilation gas delivered to the patient without information regarding duration of time that the one or more valves are in the deliver configuration.

7. The ventilator of claim 1, wherein the controller is configured for monitoring pressure within the storage vessel while ventilation gas is delivered to the patient from the storage vessel over time to determine a derivative of the pressure with respect to time until the derivative drops to a predetermined threshold approaching zero, whereupon the controller actuates the one or more valves to close the inhalation line to discontinue delivery of ventilation gas to the patient from the storage vessel.

8. The ventilator of claim 1, wherein the one or more valves are configured such that, in the delivery configuration, the inhalation line is only exposed to ventilation gas within the storage vessel and isolated from the source of pressurized gas.

9. The ventilator of claim 1, wherein the one or more valves comprise a three-port, two-position valve coupled between the source line and the inhalation line.

10. The ventilator of claim 1, wherein the valve one or more valves comprise a first valve coupled to the source line for opening and closing the source line and a second valve coupled to the inhalation line for opening and closing the inhalation line.

11. The ventilator of claim 1, wherein the compressor is configured to operate substantially continuously to draw ambient air into the source line under pressure.

12. The ventilator of claim 1, wherein the source of pressurized gas further comprises a source of one or more of pure oxygen and pressurized air.

13. The ventilator of claim 1, wherein the source of pressurized gas further comprises:
a connector for coupling an external source of pressurized gas to the ventilator; and a control valve coupled to the connector for selectively delivering pressurized gas from the external source to either an inlet of the compressor or the source line.

14. The ventilator of claim 1, further comprising a restrictor in the inhalation line for limiting a flow rate of ventilation gas from the storage vessel to the patient.

15. The ventilator of claim 1, further comprising a restrictor in the source line between an outlet of the source of pressurized gas and the one or more valves for limiting the pressure of ventilation gas delivered to the one or more valves from the source line.

16. The ventilator of claim 1, further comprising a second patient pressure sensor coupled to the inhalation line for detecting pressure in the inhalation line, the controller coupled to the patient pressure sensor for monitoring pressure in the inhalation line to determine when the patient initiates inhalation, whereupon the controller directs the one or more valves to the delivery configuration.

17. The ventilator of claim 1, wherein the compressor is configured for delivering a maximum pressure to the source line of at least 350 cm $H_2O$ (5 psi).

18. The ventilator of claim 17, further comprising a restrictor in the inhalation line, the restrictor limiting the maximum pressure of ventilation gas delivered to the patient from the storage vessel to no more than sixty centimeters of water (60 cm $H_2O$).

19. A ventilator comprising:
a housing;
a source of pressurized gas comprising a compressor within the housing;
a pre-fill vessel within the housing;
a storage vessel within the housing;
one or more valves within the housing communicating with the compressor via a source line, communicating with the pre-fill and storage vessels, and communicating with an inhalation line;
a patient circuit external to the housing and communicating with the inhalation line via tubing for delivering ventilation gas into a patient's airway, the patient circuit comprising an expiratory block including an exhale valve configured to open to the atmosphere during exhalation by the patient and close during inhalation by the patient; and
a controller coupled to the one or more valves for selectively directing the one or more valves between a delivery configuration where ventilation gas is delivered from the storage vessel into the patient's airway under positive pressure via the inhalation line and pressurized gas is delivered from the compressor to the pre-fill vessel, and a storage configuration where pressurized gas is delivered from the compressor and the pre-fill vessel into the storage vessel to store pressurized gas in the storage vessel during exhalation by the patient.

20. The ventilator of claim 19, wherein the one or more valves define a first flow path in the storage configuration communicating between the storage vessel and the compressor and pre-fill vessel for delivering pressurized gas from the compressor with the storage vessel isolated from the inhalation line and the pre-fill vessel into the storage vessel and defining second and third flow paths in the delivery configuration, the second flow path communicating between the storage vessel and inhalation line to deliver ventilation gas within the storage vessel into the patient's airway via the inhalation line, and the third path communicating between the source of pressurized gas and the pre-fill vessel for delivering pressurized gas into the pre-fill vessel.

21. The ventilator of claim 19, further comprising:
a vessel pressure sensor coupled to the storage vessel for detecting pressure of ventilation gas within the storage vessel,
wherein the controller is coupled to the vessel pressure sensor for detecting a first pressure within the storage vessel when the one or more valves are directed to the delivery configuration and detecting subsequent pressure within the storage vessel at one or more time intervals thereafter, the controller determining the volume of ventilation gas delivered to the patient based at least in part on a difference between the first pressure and the subsequent pressure.

22. The ventilator of claim 19, wherein the compressor operates substantially continuously while the one or more valves are directed between the storage configuration and the delivery configuration.

23. The ventilator of claim 19, wherein the patient circuit comprises an endotracheal tube.

24. A portable ventilator comprising:
a housing;
a power source within the housing;
a compressor within the housing operating substantially continuously during operation of the portable ventilator to draw ambient air into a source line under pressure;
a storage vessel within the housing;
a first pressure sensor coupled to the storage vessel for detecting pressure of ventilation gas within the storage vessel;
one or more valves communicating with the compressor via the source line, communicating with the storage vessel, and communicating with an inhalation line for delivering ventilation gas into a patient's airway;
a patient circuit external to the housing and communicating with the inhalation line via tubing for delivering the ventilation gas into the patient's airway, the patient circuit comprising an expiratory block including an exhale valve configured to open to the atmosphere during exhalation by the patient and close during inhalation by the patient; and
a controller coupled to the one or more valves for selectively directing the one or more valves between a storage configuration where ventilation gas is delivered from the compressor into the storage vessel with the storage vessel isolated from the inhalation line, and a delivery configuration where ventilation gas is delivered from the storage vessel into the patient's airway via the inhalation line and the patient circuit, the controller coupled to the first pressure sensor for detecting a first pressure within the storage vessel when the one or more valves are directed to the delivery configuration, and detecting subsequent pressure thereafter while ventilation gas is delivered from the storage vessel into the patient's airway via the inhalation line and the patient circuit, the controller determining the volume of ventilation gas delivered into the patient's airway based at least in part on the difference between the first pressure and the subsequent pressure.

25. A method for ventilating a patient having an airway using a ventilator in fluid communication with the patient's airway via an inhalation line of the ventilator, the ventilator comprising a storage vessel and a pre-fill vessel therein and a compressor within a housing, the method comprising:
operating the compressor to draw ambient air into the ventilator to provide pressurized air; and alternately:
a) operating the ventilator in a storage configuration where pressurized air is delivered from the compressor and the pre-fill vessel into the storage vessel to store pressurized air in the storage vessel; and
b) operating the ventilator in a delivery configuration where pressurized air is delivered from the storage vessel into the patient's airway via the inhalation line and pressurized air is delivered from the compressor into the pre-fill vessel.

26. The method of claim 25, wherein, in the delivery configuration, the inhalation line is only exposed to pressurized air within the storage vessel and isolated from the compressor.

27. The method of claim 25, wherein the compressor operates substantially continuously to draw ambient air into the ventilator under pressure during both steps a) and b).

28. The method of claim 25, further comprising repeating steps a) and b) one or more times.

29. The method of claim 25, further comprising sensing that the patient is attempting to inhale, whereupon one or more valves of the ventilator are directed to the delivery configuration to deliver pressurized air from the storage vessel into the patient's airway via the inhalation line.

30. The method of claim 29, further comprising sensing that the patient is attempting to exhale, whereupon one or more valves of the ventilator are directed to the storage configuration to isolate the storage vessel from the inhalation line and recharge the storage vessel from the compressor and pre-fill vessel.

31. The method of claim 29, wherein after a predetermined inhalation time, the ventilator is directed to the storage configuration to isolate the storage vessel from the inhalation line and recharge the storage vessel from the compressor and pre-fill vessel.

* * * * *